United States Patent [19]

Deeba

[11] Patent Number: 4,918,234

[45] Date of Patent: Apr. 17, 1990

[54] SHAPE SELECTIVE CATALYSTS FOR $C_2$ TO $C_4$ ALKANOL AMINATION

[75] Inventor: Michel Deeba, North Brunswick, N.J.

[73] Assignee: Air Products and Chemicals, Inc.

[21] Appl. No.: 108,256

[22] Filed: Oct. 13, 1987

[51] Int. Cl.$^4$ ............................................. C07C 85/06
[52] U.S. Cl. ................................................... 564/480
[58] Field of Search ................................ 564/479, 480

[56] References Cited

U.S. PATENT DOCUMENTS

| | | | |
|---|---|---|---|
| 3,384,667 | 5/1968 | Hamilton | 260/585 |
| 3,475,344 | 10/1969 | Adam et al. | 252/432 |
| 4,082,805 | 4/1978 | Kaeding | 260/585 |
| 4,398,041 | 8/1983 | Cochran et al. | 564/479 |
| 4,458,092 | 7/1984 | Deeba et al. | 564/479 |
| 4,495,369 | 1/1985 | Werner et al. | 564/480 |

FOREIGN PATENT DOCUMENTS

| | | | |
|---|---|---|---|
| 0211552 | 2/1987 | European Pat. Off. | 564/480 |
| 57-169444 | 10/1982 | Japan | 564/480 |
| 8201523 | 11/1982 | Netherlands | 564/480 |

*Primary Examiner*—James H. Reamer
*Attorney, Agent, or Firm*—Russell L. Brewer; James C. Simmons; William F. Marsh

[57] ABSTRACT

This invention relates to the catalytic preparation of $C_2$ to $C_4$ alkyl amines by the reaction of a $C_{2-4}$ alkanol with ammonia in the presence of hydrogen, the reaction being carried out utilizing a crystalline alumino-silicate catalyst system where the ions in the crystalline alumino-silicate catalyst system are predominately cobalt or nickel.

7 Claims, No Drawings

SHAPE SELECTIVE CATALYSTS FOR $C_2$ TO $C_4$ ALKANOL AMINATION

TECHNICAL FIELD

This inventions relates to an improved process for producing $C_2$ to $C_4$ alkyl amines by the reaction of an alkanol with ammonia.

BACKGROUND OF THE INVENTION

The catalyzed reaction of alkanols and ammonia to produce mono, di, and trialkyl amines is well known in the art. Typically this is accomplished by the use of a silica-alumina catalyst. Higher alkyl amines often are produced using a hydrogenation catalyst, e.g. cobalt or nickel, deposited upon silica and the reaction carried out in the presence of hydrogen. The following patents illustrate various preparations for the manufacture of alkyl amines using various catalyst systems.

U.S. Pat. No. 4,458,092 discloses the preparation of methylamines by the reaction of methanol and ammonia using a highly acidic, dehydrated alumino-silicate catalyst. Rare earth and hydrogen exchange mordenites and zeolites were representative catalysts.

U.S. Pat. No. 4,398,041 discloses the process for producing $C_1$ to $C_4$ alkylamines by the reaction of the $C_1$-$C_4$ alkanol with ammonia using a shape selective crystalline alumino-silicate zeolite catalyst.

U.S. Pat. No. 3,384,667 disclosed a process for producing primary and secondary amines in preference to tertiary amines by reacting ammonia with an alcohol in the presence of a dehydrated crystalline alumino-silicate having pores of a size to selectively yield the primary and secondary amines. The patent also discloses that the crystalline alumino-silicates can be exchanged with a variety of metal cations.

U.S. Pat. No. 4,082,805 discloses a process for producing aliphatic amines using a crystalline alumino-silicate of a ZSM-5, 11 or 21 type at temperatures from about 300°–500° C. by the reaction of a $C_1$ to $C_5$ alcohol with ammonia.

U.S. Pat. No. 3,475,344 discloses a process for producing amines by the reaction of alkanols with ammonia in the presence of hydrogen. A cobalt containing catalyst is utilized.

SUMMARY OF THE INVENTION

This invention relates to an improvement in a process for producing $C_2$ to $C_4$ alkylamines by the reaction of a $C_2$ to $C_4$ alkanol with ammonia in the presence of hydrogen and a catalyst. The improvement resides in utilizing a catalyst system comprising a crystalline alumino-silicate which has intracrystalline pores of sufficient diameter to pass the reactants and alkylamine products and the crystalline alumino-silicate having a predominate portion of the ions therein exchanged with nickel or cobalt ions.

Some of the advantages of using the process of this invention include:

an ability to produce alkylamines where the split is not equilibrium controlled, and selectivity can be altered to produce mono or di-substituted amines through shape selectivity via the intercrystalline pores of the crystalline alumino-silicate zeolite catalyst;

an ability to produce higher aliphatic amines without substantial conversion to by-product olefin; and an ability to operate at modest temperatures.

DETAILED DESCRIPTION OF THE INVENTION

The process of this invention is particularly adapted for the production of $C_2$ to $C_4$ alkylamines by the catalytic reaction of $C_2$ to $C_4$ alkanols, i.e. ethanol, isopropanol, and isobutanol. Each of these alkanols is subject to dehydration at conventional reaction temperatures and, in the past, conversion of the reactant to olefin has been high in these catalytic processes. In the process of this invention, the catalyst is one that has a pore size sufficient to permit entry of the reactant and exit of the product. Shape selectivity is a desirable feature of the zeolite catalyst and permits entry of the reactant and exit of the desired product. If the catalyst is selected with a particular intracrystalline pore size, one can enhance selectivity and reduce the amount of by-product formed. This is particularly the case where the desired product may be a mono or di-substituted amine and tri-substituted amines are undesirable. Examples of crystalline alumino-silicate zeolites suited for practicing the invention are mordenite and Y zeolite.

Crystalline alumino-silicate zeolites are prepared from alkali metal salts and typically sodium is the alkali metal. As is known, the alkali metal can be exchanged with other metal cations or replaced with a hydrogen ion by initially exchanging with ammonia and then heating or through contact with acid. In contrast to the crystalline alumino-silicates used for conventional amination reactions, the catalysts are exchanged with cobalt or nickel as the metal cation rather than alkali metal ion or hydrogen ion. Sufficient exchange should be carried out such that at least 50% of the replaceable ions in the crystalline alumino-silicate are replaced with cobalt or nickel ions and preferably at least 90% of the replaceable ions are replaced with cobalt or nickel.

In carrying out the process, the mole ratio of ammonia to alcohol in the feed stream may range from about 0.5:1 to about 12:1 and preferably should range in a mole ratio of about 1.5 to 2.5:1 moles ammonia to alcohol. The mole ratio of hydrogen to alcohol should range from 0.5 to 10 moles hydrogen per mole of alcohol, preferably 1–3 moles hydrogen per mole of alcohol.

The reaction temperatures for carrying out the process range from about 170°–220° C. Higher temperatures result in dehydration of the alcohol and form olefin by-product.

The pressure utilized in the process ranges between about 1 to 50 atm. with the pressure usually ranging from about 10 to 30 atm. In general, flow rates (GHSV) range from about 500 to 30,000 cc of alcohol per cc of catalyst per hour, and preferably from about 1,000–2,000 cc/cc/hr. The space velocity also may be used as a mechanism for reaction control to yield or a given product slate.

The following examples are provided to illustrate various embodiments of the invention and are not intended to restrict the scope thereof.

EXAMPLE 1

Preparation of Crystalline Alumino-silicate

A sodium Y zeolite in the form of ⅛" extrudate obtained from a commercial source under the trademark LZ-Y52 was exchanged in conventional manner using nickel nitrate and cobalt nitrate salts. More specifically, a 50 gram portion of LZ-Y52 Y zeolite with 0.2 moles of either nickel nitrate or cobalt nitrate dissolved in 2 liters of distilled water was used for the exchange. Temperatures of 50° C. were used for 2 hours. After stirring, each catalyst was filtered and then washed with distilled water at 50° C. for two hours and finally dried at 100° C. under an air atmosphere. Each catalyst was then reduced in a hydrogen atmosphere at 300° C. in situ. The nickel content of the nickel Y zeolite was 6.5% and the cobalt content of the cobalt Y zeolite was 5%.

EXAMPLE 2

Amination of Ethanol

The gas phase amination of ethanol was carried out using the cobalt-Y zeolite of Example 1 identified as Co-Y zeolite. The reaction was carried out over 6 cc's of catalyst at a pressure of 280 psig, a gas hourly space velocity of 1400 cc per cc catalyst per hour and using a molar feed ratio of ammonia of 2:1:2 of ammonia to ethanol to hydrogen. The temperature was varied between 170° and 210°.

Comparisons were made in the amination of ethanol to conventional cobalt on silica catalysts (CoSiO$_2$) and to the highly acidic hydrogen Y zeolite (H-Y zeolite).

Table 1 below sets forth the runs, the catalysts used, the temperatures, mole ratios employed during the reaction, along with the percent ethanol conversion and percent amine selectivity.

runs 2 and 4 are compared, it should be noted only 2.5% triethylamine is formed on Co-Y zeolite compared to about 14% in the case of cobalt on silica. The enhanced selectivity to mono- and diamines and diminished selectivity to triamine in runs 2 and 3 vs. runs 9 and 4, respectively, result from steric constraints imposed on the amination reaction by the crystalline zeolite structure. However, H-Y zeolite is ineffective for the production of amines at the temperature of the reaction. Most of the ethanol is converted to olefin. Higher temperatures result in amine formation, but also result in even higher selectivity to olefin formation.

The lower conversion levels obtained using the Co-Y zeolite is attributed to the lower concentration of cobalt in the zeolite pores. The cobalt concentration amounts to about 5% by weight compared to 25% by weight in case of cobalt on silica. However, the Co-Y zeolite is much more active than cobalt on silica if the activity is measured per unit metal content.

EXAMPLE 3

Amination of Isobutanol

The procedure of Example 2 was followed except isobutanol was substituted for ethanol. Several cobalt and nickel catalysts were compared with Co-Y zeolite for aminating isobutanol. Nickel or cobalt catalysts supported on silica or alumina showed the same amines

TABLE 1

Amination of Ethanol Over Cobalt on Silica and Co—Y Zeolite as a Function of Temperature (280 psi, N/R/H = 2/1/2)

| Runs | Catalyst | Temp. (°C.) | N/R/H | GHSV | % Ethanol Converted | % Amine Selectivity (wt.) | | |
|---|---|---|---|---|---|---|---|---|
| | | | | | | MEA | DEA | TEA |
| 1 | Co—Y Zeolite | 190 | 2/1/2 | 1400 | 50.0 | 77.2 | 21.8 | 1 |
| 2 | Co—Y Zeolite | 200 | 2/1/2 | 1400 | 63.3 | 69.0 | 28.5 | 2.5 |
| 3 | Co—Y Zeolite | 210 | 2/1/2 | 1400 | 70.9 | 57.6 | 37.4 | 5.4 |
| 4 | Co/SiO$_2$ | 170 | 2/1/2 | 1400 | 56.3 | 46.0 | 39.4 | 14.1 |
| 5 | Co/SiO$_2$ | 180 | 2/1/2 | 1400 | 72.5 | 36.5 | 43.1 | 19.8 |
| 6 | Co/SiO$_2$ | 190 | 2/1/2 | 1400 | 86.8 | 31.0 | 47.6 | 21.4 |
| 7 | Co/SiO$_2$ | 190 | 2/1/1 | 1400 | 80.8 | 32.9 | 47.6 | 19.5 |
| 8 | Co/SiO$_2$ | 200 | 2/1/2 | 1400 | 92.4 | 29.8 | 49.5 | 20.6 |
| 9 | Co/SiO$_2$ | 200 | 2/1/1 | 1400 | 88.0 | 30.9 | 49.2 | 19.9 |
| 10 | H—Y Zeolite | 198 | 2/1/2 | 900 | 32.4 | 0 | 0.1 | 0 |
| 11 | H—Y Zeolite | 199 | 1.5/1/0 | 740 | 39.7 | 0 | 0.02 | 0 |

(a) N/R/H: Ammonia/Ethanol/Hydrogen, mole ratio
(b) MEA: Monoethylamine
(c) DEA: Diethylamine
(d) TEA: Triethylamine At equal ethanol conversion levels, the selectivity to monoethylamine obtained using Co-Y zeolite is almost twice that observed for cobalt on silica. A most interesting aspect, though, is the low formation of triethylamine, compare runs 3 and 9. The ethanol conversion is about 70% for both catalysts but, only one-fourth of the triethylamine is produced using the Co-Y zeolite. If split at the same conversion levels. A very small amount of triisobutylamine was formed. The main product of the amination reaction over supported nickel or cobalt catalysts is diisobutylamine. High selectivity to the monoisobutylamine could only be obtained over the pore shape selective Co-Y zeolite. Table 2 provides reaction conditions and results.

TABLE 2

Reductive Amination of Isobutanol Over Cobalt and Nickel Supported Metals and Over Cobalt Exchanged Y-Zeolite

| Catalyst | % Metal | % Isobutanol Conversion at Temp., °C. | | | | |
|---|---|---|---|---|---|---|
| | | 170 | 180 | 190 | 200 | 210 |
| G-87 | Ni = 40 | 38.7 (63.6;34.9;t) | 59.9 (43.3;55.7;t) | 77.3 (24.7;74.8;t) | 92.5 (17.1;80.8;1.5) | |
| G-65 | Ni = 25 | | | 57.0 (40.6;58.2;0) | 78.7 (25.2;73.4;0) | 87.5 (19.8;80.0;.4) |
| Ni/Al$_2$O$_3$ | Ni = 33 | 35.4 (72.3;27;0) | 54.1 (53.8;46.0;0) | 74.5 (31.1;68;7) | 86.7 (23.2;75;0.5) | |
| 7% Co/SiO$_2$ | Co = 7% | | | 22.6 (69.2,10.5,0) | | |
| Co—Y | Co = 5 | | | 43.2 | 52.6 | 64.0 |

TABLE 2-continued

Reductive Amination of Isobutanol Over Cobalt and
Nickel Supported Metals and Over Cobalt Exchanged Y-Zeolite

| Catalyst | % Metal | % Isobutanol Conversion at Temp., °C. | | | | |
|---|---|---|---|---|---|---|
| | | 170 | 180 | 190 | 200 | 210 |
| | | | | (90.0;9.1;0) | (84.6;14.8;0) | (73.6;25.9;0) |

Number above parentheses pertains to percent conversion.
Numbers between parentheses indicate the amines split to mono-, di-, and tri-isobutylamine.
G-87 refers to Girdler 87 catalyst designation.
G-65 refers to Girdler 65 catalyst designation.
t = trace The selectivity to diisobutylamine over the supported nickel or cobalt catalyst is favored with an increase in the isobutanol conversion. At about 50% isobutanol conversion the formation of diisobutylamine is favored over mono-substituted amine. On the other hand, the selectivity to monoisobutylamine over Co-Y zeolite is almost twice that observed for nickel or cobalt catalysts supported on silica or alumina. The reverse is true for the disubstituted amine. Over Co-Y zeolite at all isobutanol conversion levels the monoisobutylamine product is favored over the disubstituted amine.

What is claimed is:

1. In the catalytic preparation of $C_{2-4}$ alkylamines by the reaction of a $C_{2-4}$ alkanol with ammonia in the presence of hydrogen, the improvement which comprises: utilizing a crystalline alumino-silicate Y zeolite as the catalyst where such Y zeolite has a predominant proportion of the cations replaced with cobalt or nickel ions and utilizing ethanol as the alkanol.

2. In the catalytic preparation of $C_{2-4}$ alkylamines by the reaction of a $C_{2-4}$ alkanol and ammonia in the presence of hydrogen, the improvement which comprises utilizing isobutanol as said alkanol and carrying out the reaction in the presence of a cobalt exchanged Y zeolite where the mole ratio of hydrogen to isobutanol is from 0.5 to 10:1 and the mole ratio of ammonia to alkanol is from 0.5 to 6:1.

3. The process of claim 1 wherein the gas hourly space velocity ranges from 500 to 30,000 cc/cc of alcohol per cc catalyst/hour.

4. The process of claim 1 wherein the mole ratio ammonia to $C_{2-4}$ alkanol is from 0.5 to 6:1.

5. The process of claim 4 wherein the mole ratio of hydrogen to $C_{2-4}$ alkanol is from 0.5 to 10:1.

6. The process of claim 5 wherein the alkanol is ethanol and the temperature ranges from 170°–220° C.

7. The process of claim 5 wherein the alkanol is isobutanol and monoisobutylamine is produced in high selectivity.

* * * * *